(12) United States Patent
Jung et al.

(10) Patent No.: US 9,535,035 B2
(45) Date of Patent: Jan. 3, 2017

(54) ANALYSIS DEVICE AND ANALYSIS METHOD USING THE SAME

(71) Applicant: Electronics and Telecommunications Research Institute, Daejeon (KR)

(72) Inventors: Moon Youn Jung, Daejeon (KR); Seungkyoung Yang, Daejeon (KR); Kibong Song, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 253 days.

(21) Appl. No.: 13/949,069

(22) Filed: Jul. 23, 2013

(65) Prior Publication Data

US 2014/0178900 A1 Jun. 26, 2014

(30) Foreign Application Priority Data

Dec. 26, 2012 (KR) .................. 10-2012-0153424

(51) Int. Cl.
*G01N 27/74* (2006.01)
*G01N 33/543* (2006.01)
*B82Y 25/00* (2011.01)
*H01F 41/30* (2006.01)

(52) U.S. Cl.
CPC ............ *G01N 27/745* (2013.01); *B82Y 25/00* (2013.01); *G01N 33/54326* (2013.01); *G01N 33/54366* (2013.01); *H01F 41/309* (2013.01)

(58) Field of Classification Search
CPC .... B82Y 25/00; B82Y 35/00; C12Q 2563/143
See application file for complete search history.

(56) References Cited

U.S. PATENT DOCUMENTS

| | | | |
|---|---|---|---|
| 2003/0203507 A1* | 10/2003 | Liberti et al. ................. | 436/526 |
| 2007/0290683 A1* | 12/2007 | Ikeda et al. ................... | 324/260 |
| 2008/0284413 A1* | 11/2008 | Tsukamoto ...... | G01N 33/54333 324/204 |
| 2009/0205201 A1* | 8/2009 | Xu et al. .......................... | 29/825 |
| 2009/0216082 A1* | 8/2009 | Rabinovitz ................... | 600/118 |
| 2009/0325258 A1* | 12/2009 | Matsunaga et al. .......... | 435/174 |
| 2011/0244484 A1* | 10/2011 | Chae et al. .................. | 435/7.21 |

FOREIGN PATENT DOCUMENTS

KR 10-2011-0024846 A 3/2011

* cited by examiner

*Primary Examiner* — Rebecca Martinez

(57) ABSTRACT

Provided are an analysis device and an analysis method. According to the device and the method, a giant magnetoresistance (GMR) sensor unit is formed to be the same as the size of one cancer cell or smaller and magnetic resistance according to the number of magnetic nano particles coupled with the one cancer cell by using the GMR sensor unit, thereby not only diagnosing cancer but also simply and cheaply distinguishing the type of the cancer.

12 Claims, 11 Drawing Sheets

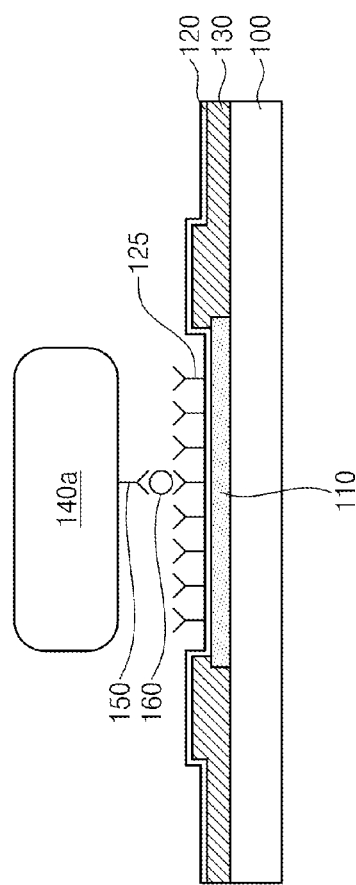
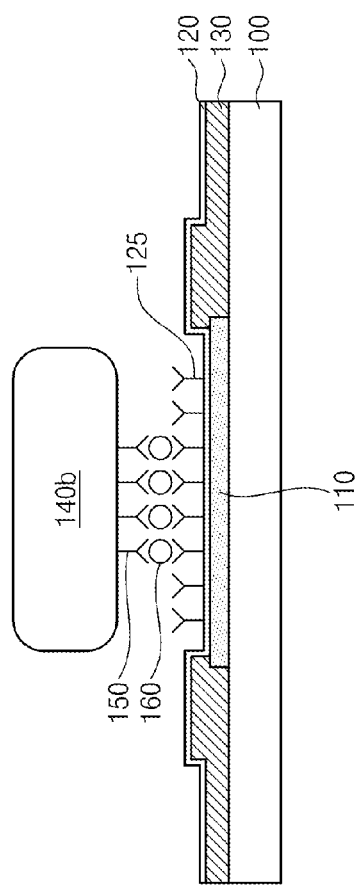

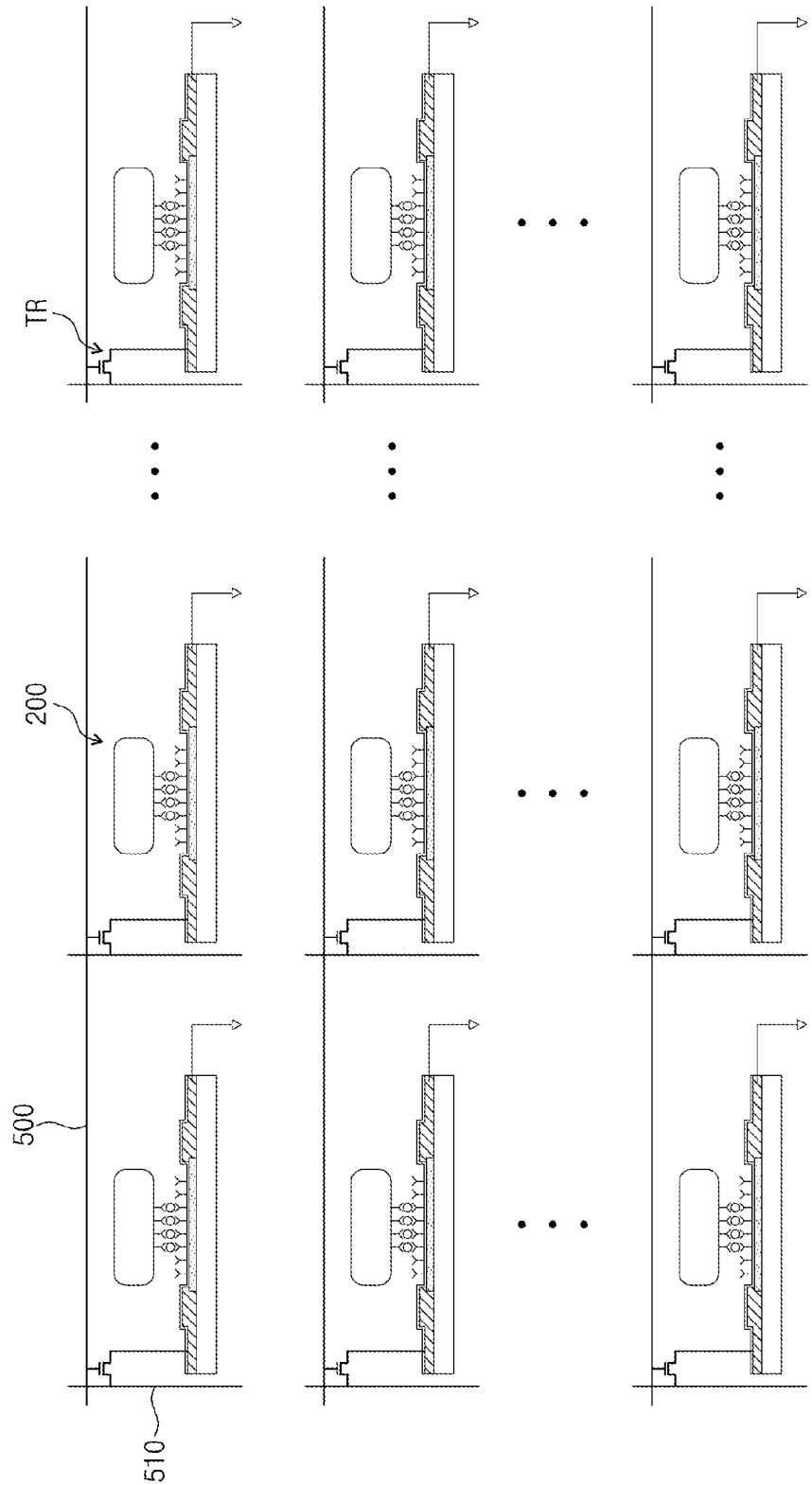

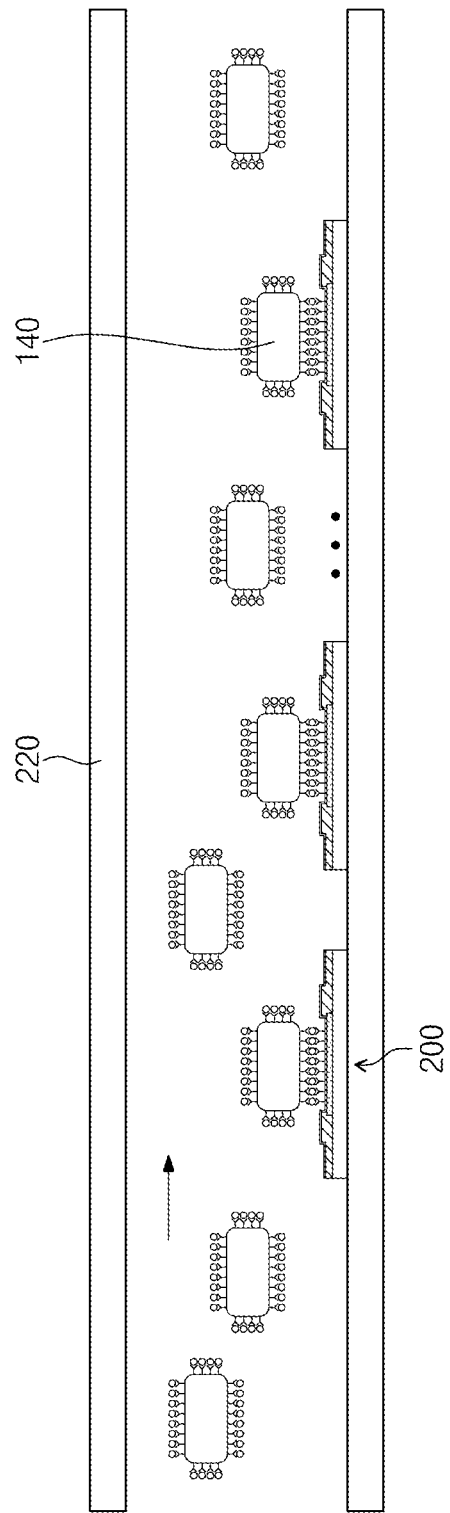

ANALYSIS DEVICE AND ANALYSIS METHOD USING THE SAME

CROSS-REFERENCE TO RELATED APPLICATIONS

This U.S. non-provisional patent application claims priority under 35 U.S.C. §119 of Korean Patent Application No. 10-2012-0153424, filed on Dec. 26, 2012, the entire contents of which are hereby incorporated by reference.

BACKGROUND OF THE INVENTION

The present invention disclosed herein relates to an analysis device and an analysis method of using the same.

In the medical field, it is necessary to separate a cellular type or an intracellular constituent as a manufacturing tool for a final target or different analysis in diagnosis, treatment, and research fields. For example, it is needed to analyze a cancer cell. Blood cancer cells designate cancer cells existing in peripheral blood of a cancer patient, which are cancer cells separated from primary lesions or metastasis lesions. Such blood cancer cells are expected as an influential biomarker for cancer diagnosis, prognostic analysis, and micrometastatic analysis. In addition, compared to typical cancer diagnosis methods, since using a non-invasive method, blood cancer cell analysis is very a promising future cancer diagnosis method. However, since a proportion of blood cancer cells in blood is one cancer cell per one billion of the entire cells or one cancer cell per 106 to 107 of white blood cells, which is very low, it is difficult to precisely analyze and a very exquisite analysis method is necessary.

Although various methods have been researched as a method of separating cancer cells from blood, much time is necessary to check, only information on existence and an amount of cancer cells and is provided, and it is difficult to analyze a type of cancer. Also, an interference caused by aspecific-coupled blood cells occurs.

SUMMARY OF THE INVENTION

The present invention provides a device for analyzing material species including biomaterial.

The present invention also provides a method of analyzing material species including biomaterial.

Embodiments of the present invention provide analysis device including a giant magnetoresistance (GMR) sensor unit on a substrate, a receptor on the GMR sensor unit, a target particle captured by the receptor and comprising magnetic nano particles, and electrodes in contact with both ends of the GMR sensor unit. A width of the GMR sensor unit is the same as a width of the target particle or smaller.

In some embodiments, the device may further include a receptor-fastened layer covering the GMR sensor unit and fastening the receptor.

In other embodiments, the receptor-fastened layer may be formed of a polymer.

In still other embodiments, resistance or a signal voltage of the GMR sensor unit may be changed depending on the number of the magnetic nano particles coupled with the target particles captured by the receptor.

In even other embodiments, the target particle may be a cancer cell, and the magnetic nano particles may be attached to epithelial cellular adhesion molecule (EpCAM) expressed in a cellular membrane of the cancer cell.

In yet other embodiments, the cancer cell may include a different number of EpCAMs according to a type thereof, and the number of the magnetic nano particles corresponding the number of EpCAMs may be coupled with the cancer cell.

In further embodiments, sensitivity S of the GMR sensor unit and a distance R from a surface of the GMR sensor unit to a certain point may satisfy following Equation 1

$$S \propto 1/R^3 \qquad \text{Equation (1)}$$

In still further embodiments, the device may further include one selection device connected to one end of the GMR sensor unit, in which one GMR sensor unit and the one selection device may form one unit analysis cell, and the analysis device may include a plurality of unit analysis cells.

In even further embodiments, the unit analysis cells may be arranged in an array.

In yet further embodiments, the device may further include a channel through which a mixed solution including the target particle flows, the channel in which the GMR sensor unit and the electrodes are arranged.

In much further embodiments, the mixed solution may be blood, and the target particle may be a blood cancer cell.

In still much further embodiments, the selection device may be one of a transistor and a diode.

In other embodiments of the present invention, analysis methods include manufacturing an analysis device comprising a GMR sensor unit on a substrate, a receptor on the GMR sensor unit, and electrodes in contact with both ends of the GMR sensor unit, coupling a target particle desired to be captured by using the receptor, with magnetic nano particles, capturing one target particle on the GMR sensor unit by using the receptor, and measuring resistance or a signal voltage of the GMR sensor unit.

In some embodiments, the method may further include forming a database by researching a variance in the resistance or the signal voltage of the GMR sensor unit depending on the number of the magnetic nano particles coupled with the target particle.

In other embodiments, a width of the GMR sensor unit may be the same as a width of the target particle or smaller.

In still other embodiments, the target particle may be a cancer cell, the magnetic nano particles may be attached to epithelial cellular adhesion molecule (EpCAM) expressed in a cellular membrane of the cancer cell, and the capturing the target particle by using the receptor may be performed by using an antigen-antibody sandwich-coupling method.

In yet other embodiments, the method may further include, before the capturing the target particle by using the receptor, forming a database by researching a variance in the resistance or the signal voltage of the GMR sensor unit depending on the number of the magnetic nano particles coupled with the target particle.

In further embodiments, the manufacturing the analysis device may include forming the GMR sensor unit on the substrate, forming the electrodes in contact with the both ends of the GMR sensor unit, and forming a receptor-fastened layer for fastening the receptor to the GMR sensor unit.

In still further embodiments, the forming the GMR sensor unit may include forming a ferromagnetic film on the substrate, forming an antiferromagnetic film, and etching the antiferromagnetic film and the ferromagnetic film.

In even further embodiments, the receptor-fastened layer may be formed of a polymer layer.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 4A to 4C are views illustrating a variance in voltage of a sensor according to the number of magnetic nano particles coupled with target particles;

FIGS. 6A and 6B illustrate examples of applying the analysis device; and

FIG. 7 illustrates another example of applying the analysis device.

DETAILED DESCRIPTION OF PREFERRED EMBODIMENTS

Hereinafter, the embodiments of the present invention will be described in detail with reference to the attached drawings. However, the present invention is not limited to the embodiments but may be embodied in various shapes and may be diversely changed. However, the embodiments are described to perfectly disclose the present invention and provided to allow a person skilled in the art to fully understand the scope of the present invention. In the attached drawings, sizes of elements are enlarged rather than real sizes thereof for convenience of description and ratios of respective elements may be exaggerated or reduced.

When it is mentioned that an element is "on" or "connected to" another element, the element may be in direct contact with or connected to the other element but may be understood as still another element may exist therebetween. On the other hand, when it is mentioned that an element is "directly on" or "directly connected to" another element, it may be understood that there is no other elements therebetween. Other expressions describing relation between elements, for example, "between" or "direct between" may be understood in like manner.

Terms such as a first and a second may be used to describe various elements, but the elements are not limited to the terms. The terms are used only to distinguish one element from another element. For example, within the scope of the present invention, a first element may be designated as a second element, and similarly, the second element may be designated as the first element.

Singular expressions, as not clearly described contextually, include plural expressions. Terms such as "include" or "have" are for designating presence of features, numbers, steps, operations, elements, components, or combinations thereof mentioned in the specification, and it may be understood as one or more features, numbers, steps, operations, elements, components, or combinations thereof may be further added thereto.

Terms used in the embodiments, as not differently defined, may be understood as meanings generally known to a person skilled in the art. Also, "at least one" may be used as the same meaning as one at a minimum and may selectively designate one or more.

Figure 1A:
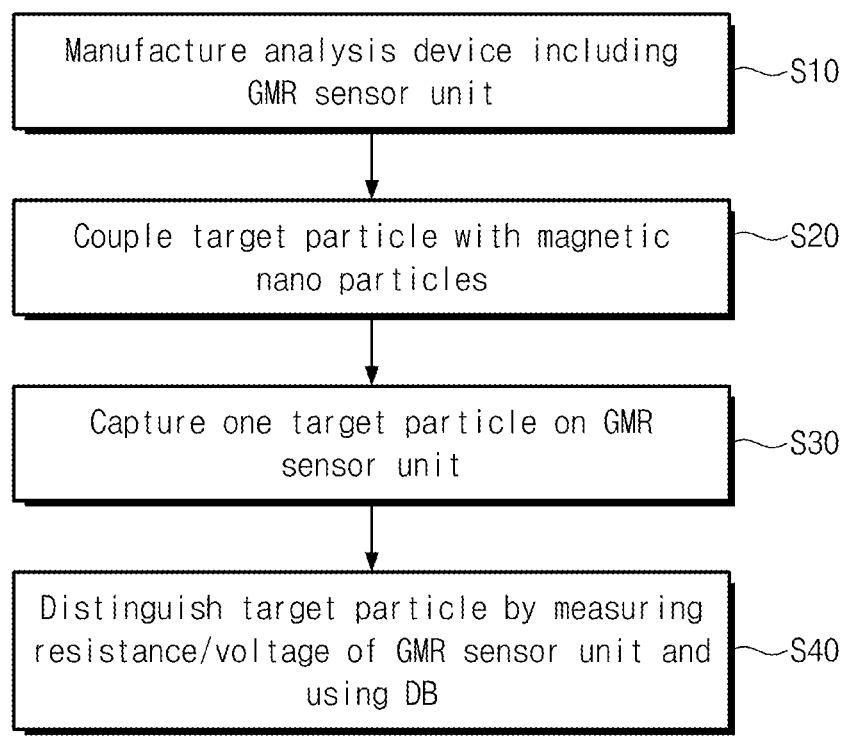
FIG. 1A is a flow chart illustrating a method of analyzing a target particle according to an embodiment of the present invention.
Figure 1B:
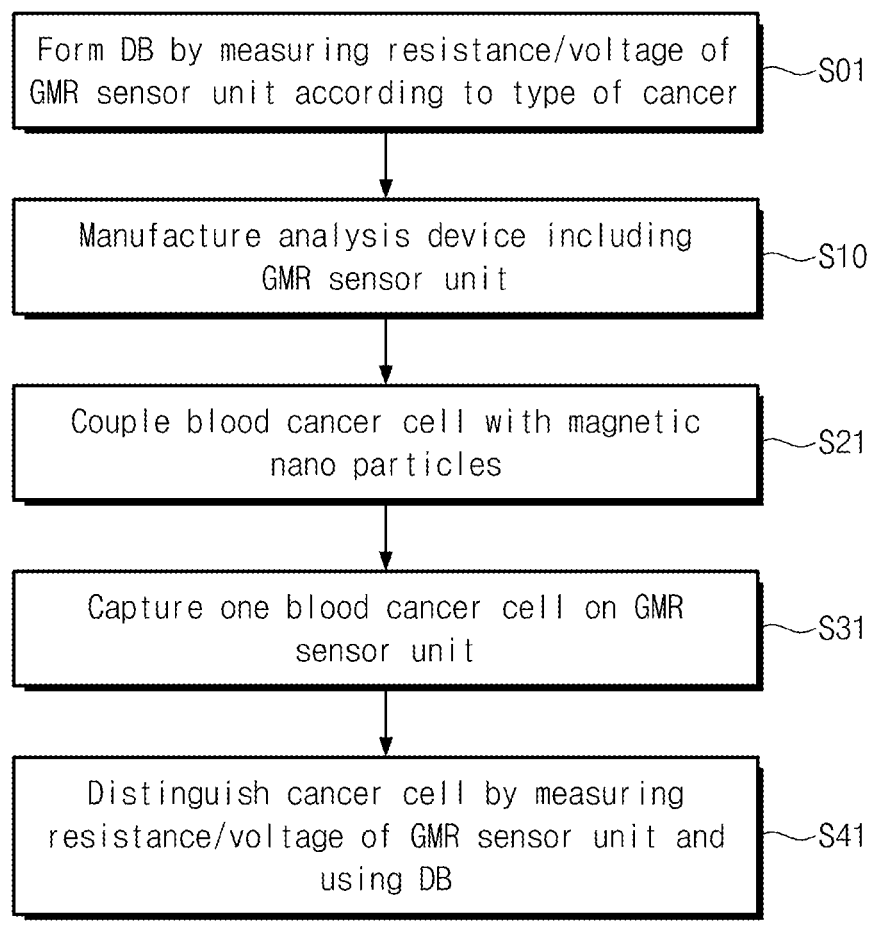
FIG. 1B is a flowchart illustrating a method of analyzing blood cancer cells according to an embodiment of the present invention.
Figure 2:
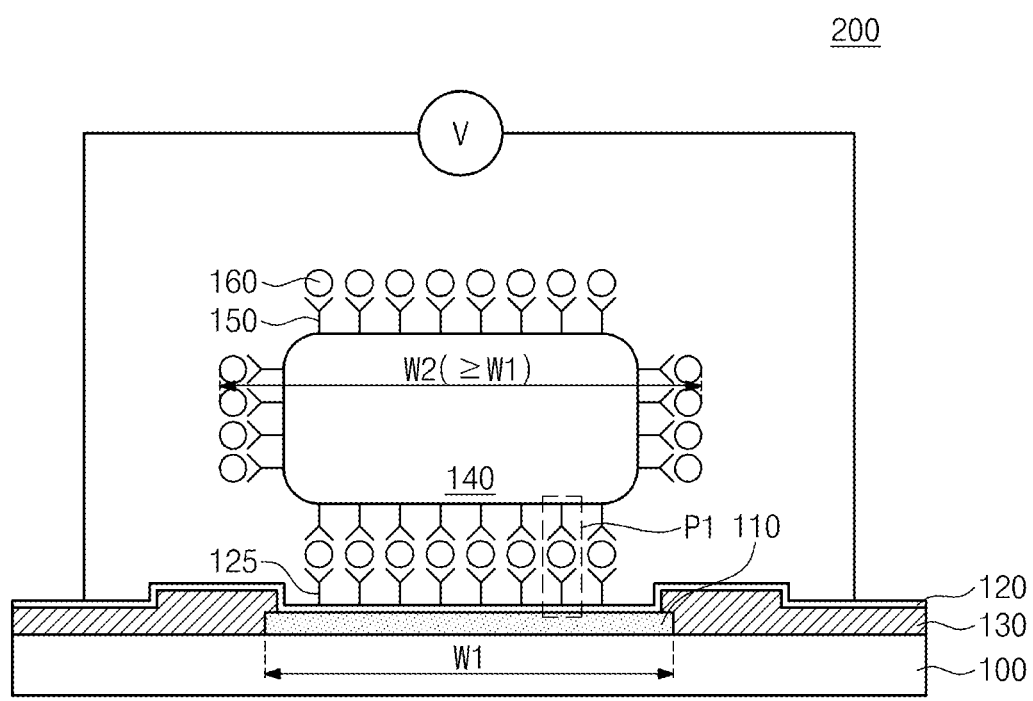
FIG. 2 is a schematic cross-sectional view illustrating an analysis device according to an embodiment of the present invention.
Figure 3A:
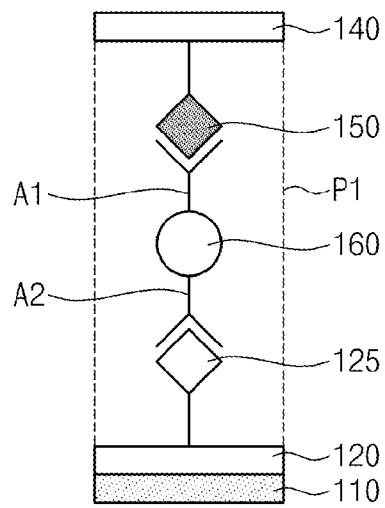
FIGS. 3A and 3B are enlarged views illustrating a part "P1" in FIG. 2.
Figure 3B:
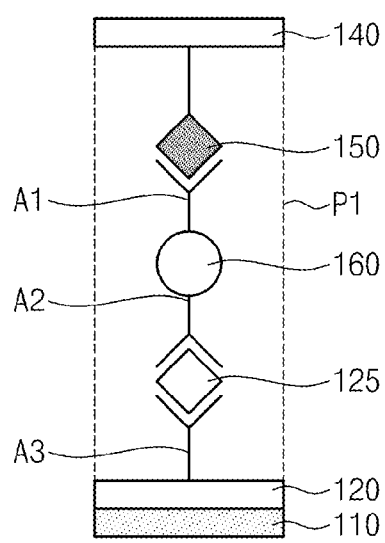

FIG. 1A is a flow chart illustrating a method of analyzing a target particle according to an embodiment of the present invention. FIG. 1B is a flowchart illustrating a method of analyzing blood cancer cells according to an embodiment of the present invention. FIG. 2 is a schematic cross-sectional view illustrating an analysis device according to an embodiment of the present invention. FIGS. 3A and 3B are enlarged views illustrating a part "P1" in FIG. 2.

Referring to FIGS. 1A and 2, the method of analyzing the target particle includes manufacturing the analysis device 200 including a giant magnetoresistance (GMR) sensor unit 110 (S10). The analysis device 200 includes the GMR sensor unit 110 on a substrate 100, electrodes 130 in contact with both ends thereof, a receptor-fastened layer 120 covering the electrodes 130, and a receptor 125 fastened to the receptor-fastened layer 120. The receptor 125 is disposed only on the receptor-fastened layer 120 overlapped with the GMR sensor unit 110. The receptor 125 may be an antigen or an antibody capable of being coupled with a marker 150 of a target particle 140 desired to be captured by using an antigen-antibody sandwich coupling method. The marker 150 of the target particle 140 is coupled with a magnetic nano particle 160.

Referring to FIGS. 1A and 2, the manufacturing the analysis device 200 (S10) may include forming the GMR sensor unit 110 on the substrate 100, forming the electrodes 130 in contact with the both ends of the GMR sensor unit 110, and forming the receptor-fastened layer 120 to which the receptor 125 is fastened, on the GMR sensor unit 110. The forming the GMR sensor unit 110 may be performed by forming a ferromagnetic film and an antiferromagnetic film on the substrate 100 by using, for example, a vapor deposition process and etching the ferromagnetic film and the antiferromagnetic film. In or after the vapor deposition process, an external magnetic field is applied to control a direction of spinning the ferromagnetic film and the antiferromagnetic film. The electrodes 130 may be formed of a conductive film. To form the GMR sensor unit 110 and the electrodes 130, a semiconductor manufacturing process such as a vapor deposition process, a photolithography process, and an etching process may be applied. The receptor-fastened layer 120 may be formed of a polymer.

A width W1 of the GMR sensor unit 110 is the same as a width W2 of the target particle 140 or smaller. Accordingly, only one target particle 140 is captured on the GMR sensor unit 110. The magnetic nano particle coupled with the target particle 140 causes a change of the external magnetic field of the GMR sensor unit 110, and accordingly, magnetic resistance of the GMR sensor unit 110 is changed, thereby changing a signal voltage between the electrodes 130. According thereto, existence of the target particle 140 may be sensed. Also, depending on the number of the magnetic nano particles 160 coupled with the target particle 140, the magnetic resistance/signal voltage of the GMR sensor unit 110 are changed, thereby distinguishing the target particle 140.

As a detailed example, referring to FIGS. 1B and 2, the present embodiment may be applied to a method of analyzing blood cancer cells. In detail, the method includes forming a database by measuring resistance/voltage of the GMR sensor unit 110 (S01), manufacturing the analysis device 200 (S10), coupling blood cancer cells with magnetic nano particles (S21), capturing one blood cancer cell on the GMR sensor unit 110 (S31), and distinguishing a cancer cell by measuring the resistance/voltage of the GMR sensor unit 110 and using the database (S41). In this case, the target particle 140 may be a blood cancer cell.

The marker 150 may be epithelial cellular adhesion molecule (EpCAM) which is expressed in a cellular membrane of the cancer cell 140. In the case of an EpCAM maker, the number of expression EpCAMs per cell of a breast-cancer cell SKB4-3 is 500,000 or less, the number of expression EpCAMs per cell of a prostate cancer cell PC3-9 is 50,000 or less, and the number of expression EpCAMs per cell of a bladder cancer cell T-24 is 2,000 or less, in which great differences are present between the numbers of the markers 150 expressed per one cancer cell depending on a cancer type. As described above, since the numbers of the markers 150 are different according to the cancer types and the magnetic nano particles 160 are coupled with the markers 150, the numbers of coupled magnetic nano particles 160 may be different according to the cancer types. Accordingly, since the size of a magnetic field is different according to the cancer type, the magnetic resistance/signal voltage of the GMR sensor unit 110 become different according thereto. The coupling the blood cancer cells with the magnetic nano particles (S21) may be performed by mixing blood and the magnetic nano particles. In this case, the blood cancer cell and the magnetic nano particles may be coupled with one another by using the antigen-antibody sandwich-coupling method.

Referring FIGS. 3A and 3B, coupling relation between the marker 150 and the receptor 125 may be diverse. For example, as shown in FIG. 3A, the marker 150 may be an antigen such as the EpCAM, which may be coupled with a first antibody A1. The first antibody A1 may be coupled with the magnetic nano particle 160, and the magnetic nano particle 160 may be coupled with a second antibody A2. The receptor 125 may be another antigen coupled with the second antibody A2. Otherwise, as shown in FIG. 3B, the receptor 125 may be another antibody, and another antigen A3 may be coupled between the receptor 125 and the receptor-fastened layer 120.

Figure 4C:
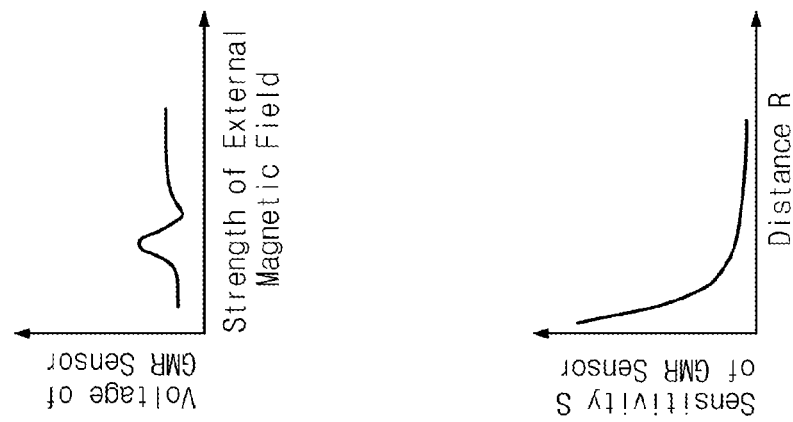
Figure 4C:
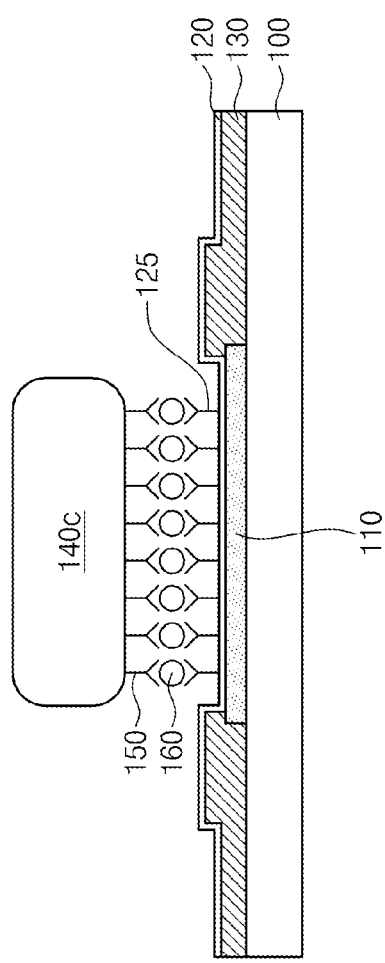

FIGS. 4A to 4C are views illustrating a variance in voltage of a sensor according to the number of magnetic nano particles coupled with target particles.

Referring to FIGS. 4A to 4C, the number of the magnetic nano particles 160 coupled with a second target particle 140b is greater than the number of the magnetic nano particles 160 coupled with a first target particle 140a and smaller than the number of the magnetic nano particles 160 coupled with a third target particle 140c. In this case, the signal voltage of the GMR sensor unit 110 may be greatest when capturing the first target particle 140a and may be smallest when capturing the third target particle 140c. The first target particle 140a may be, for example, a bladder cancer cell having a relatively smaller number of EpCAM markers or a normal cell such as a white blood cell, and the third target particle 140c may be a breast-cancer cell having a relatively greater number of EpCAM markers. The second target particle 140b may be, for example, a prostate cancer cell.

Otherwise, on the contrary, the signal voltage may become smaller as the number of the magnetic nano particles 160 is smaller.

Figure 5A:
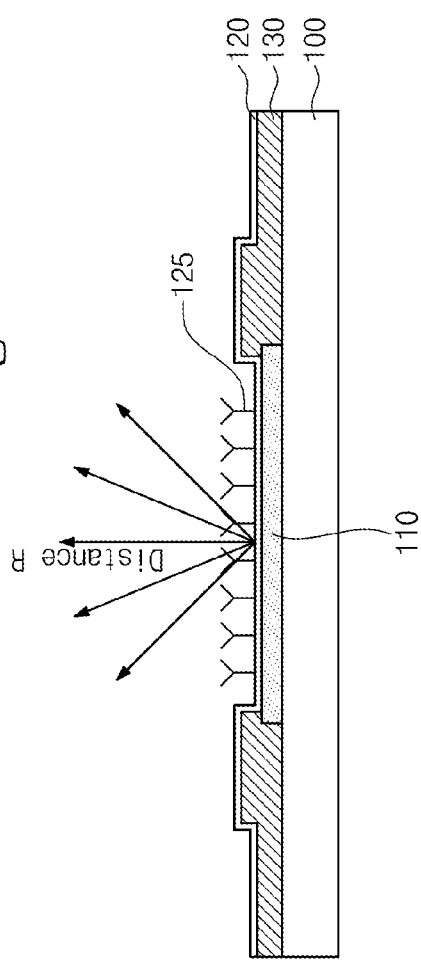
FIGS. 5A to 5C illustrate relation between a distance R from a surface of a giant magnetoresistance (GMR) sensor 110 and sensitivity of the GMR sensor 110.
Figure 5B:
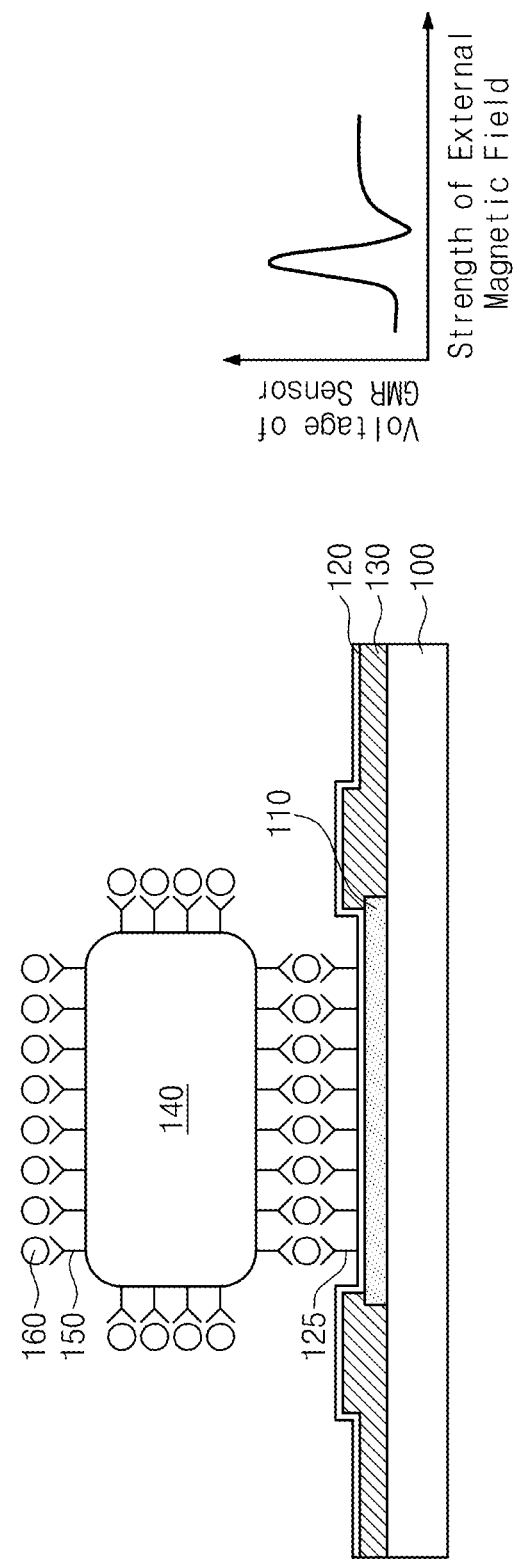
Figure 5C:
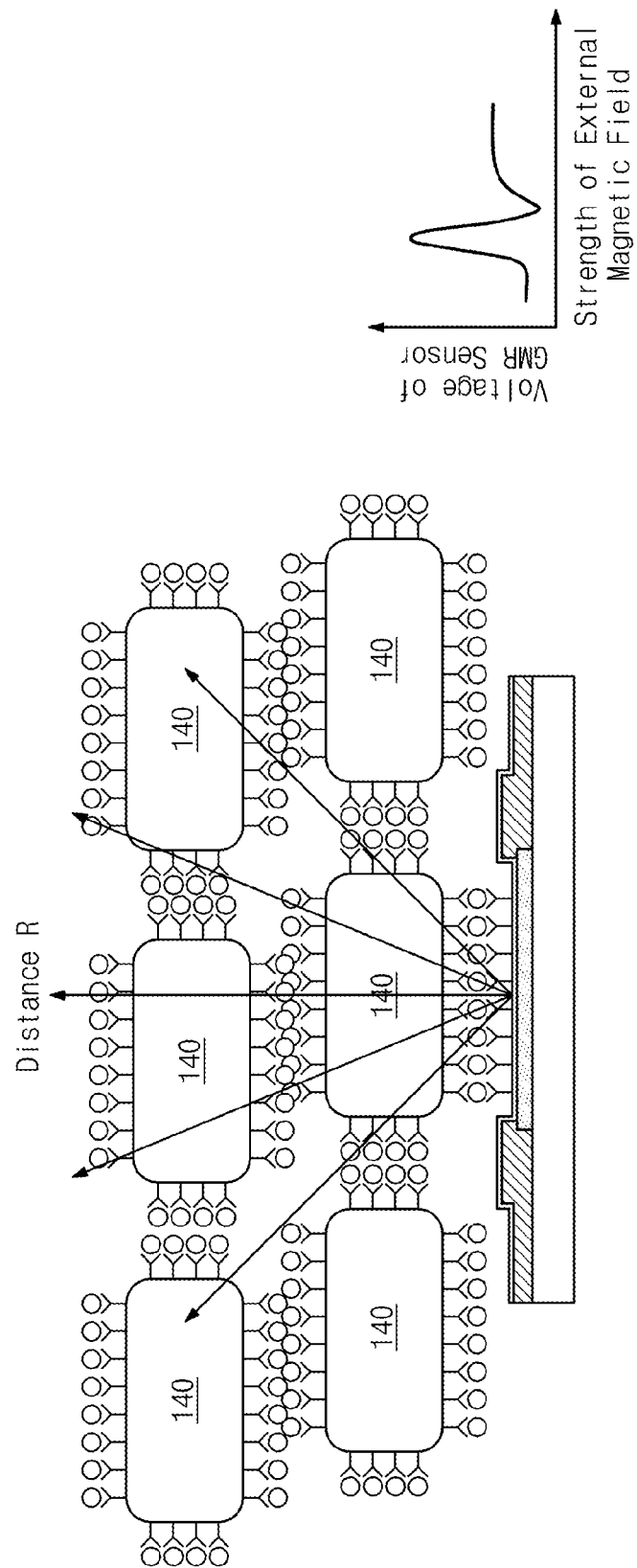

FIGS. 5A to 5C illustrate relation between a distance R from a surface of the giant magnetic resistance sensor 110 and sensitivity S of the GMR sensor 110.

Referring to FIG. 5A, the sensitivity S of the GMR sensor unit 110 and the distance R from the surface of the GMR sensor unit 110 to a certain place may satisfy the following Equation 1.

$$S \propto 1/R^3 \qquad \text{Equation (1)}$$

Referring to FIGS. 5B and 5C, since the sensitivity S is in rapidly inverse proportion to the cube of the distance R in Equation 1, the magnetic nano particles 160 coupled with one target particle 140 attached to the surface of the GMR sensor unit 110 have a predominant influence on the magnetic resistance of the GMR sensor unit 110 and an influence of other target particles attached to the one target particle 140 or the magnetic nano particles 160 coupled with the peripheral floating target particles 140 is very insignificant due to long distances from the GMR sensor unit 110. Accordingly, as shown in FIGS. 5B and 5C, the voltage of the GMR sensor unit 110 may be approximately the same when a single target particle 140 is captured or several target particles 140 are captured on the GMR sensor unit 110. That is, when one cancer cell 140 occupies the GMR sensor unit 110, although a plurality of the cancer cells 140 is crowded around the GMR sensor unit 110, there is little influence on the GMR sensor unit 110. That is, due to an effect of 1/R3, the sensitivity of the peripheral cancer cells 140 reaching the GMR sensor unit 110 becomes reduced by 1/R3.

Figure 6A:
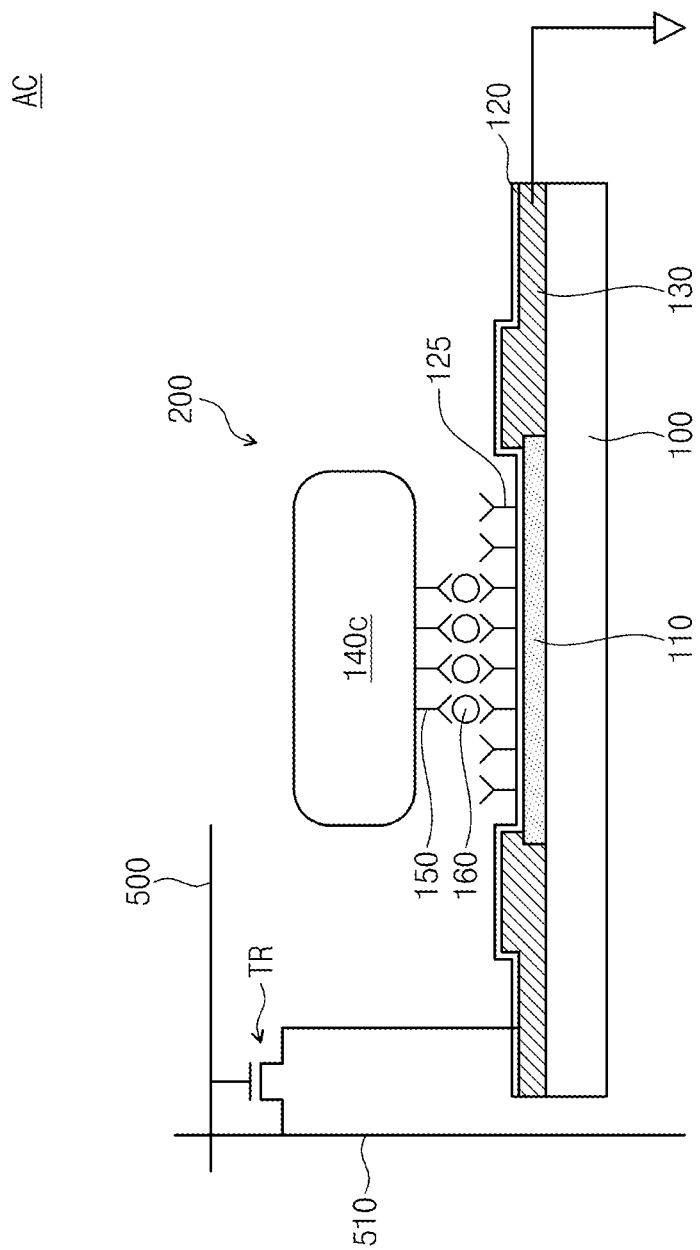

FIGS. 6A and 6B illustrate examples of applying the analysis device 200.

Referring to FIG. 6A, one of the electrodes 130 may be connected to a selection device such as a transistor TR. The transistor TR may be connected to wirings 500 and 510. As the selection device, a diode may be used in addition to the transistor TR. A single selection device TR and one analysis device 200 form a single unit analysis cell AC. Such unit analysis cell AC may be arranged in an array as shown in FIG. 6B to form a multiplexing sensor array. When being arranged in the array as described above, several cancer types may be measured at the same time.

The analysis device 200 including the GMR sensor unit 110 may be manufactured by using a semiconductor process of 100% relatively to other biosensors. Accordingly, since a highly integrated sensor array may be formed as described above, it is possible to measure and analyze a plurality of times at the same time. Also, since being formed of a large number of sensor arrays, a plurality of redundances is arranged in such a way that reliability by statistically processing sensor values may be drastically increased. When several types of cancer cells are mixed in blood, how many types of cancer cells are included in the blood may be determined by using sizes of the signal voltages of the GMR sensor unit 110 measured by the respective sensor arrays.

FIG. 7 illustrates another example of applying the analysis device.

Referring to FIG. 7, the analysis devices 200 may be arranged in an array in a channel 220 through which a mixed solution including the target particles 140 flows. The channel 200 may be, for example, a channel or a flow path of a minute fluid device. The mixed solution may be blood, and the target particle 140 may be a cancer cell. The mixed solution may be inserted into the channel 220 while being mixed with a buffer solution such as a saline solution. The target particle 140 may be captured on the analysis device 200 by using the antigen-antibody sandwich-coupling method while flowing through the channel 220. Accordingly, it is possible to cheaply and simply diagnose/distinguish cancer.

According to the analysis device and the analysis method, a GMR sensor unit is formed to be the same as the size of one cancer cell or smaller and magnetic resistance according to the number of magnetic nano particles coupled with the one cancer cell by using the GMR sensor unit, thereby not only diagnosing cancer but also simply and cheaply distinguishing the type of the cancer.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An analysis device comprising:
a giant magnetoresistance (GMR) sensor unit disposed on a substrate;
a receptor-fastened layer fastening receptors to the GMR sensor unit and disposed on the GMR sensor unit;
the receptors fastened to the receptor-fastened layer;
a target particle comprising a plurality of magnetic nano particles and a plurality of markers, at least one of the plurality of magnetic nano particles being coupled with a corresponding one of the receptors using a first antibody and being coupled with a corresponding one of the markers of the target particle using a second antibody; and
electrodes in contact with both ends of the GMR sensor unit,
wherein a width of the GMR sensor unit is the same as or smaller than a width of the target particle, and
wherein the target particle is a single particle.

2. The device of claim 1, wherein the receptor-fastened layer is formed of polymer.

3. The device of claim 1, wherein a magnetic resistance, a signal voltage of the GMR sensor unit, or both, changes depending on the number of the magnetic nano particles coupled with the target particle captured by the receptors.

4. The device of claim 3, wherein the target particle is a cancer cell, and
wherein the magnetic nano particles are attached to epithelial cellular adhesion molecules (EpCAMs) expressed in a cellular membrane of the cancer cell.

5. The device of claim 4, wherein the cancer cell comprises a different number of EpCAMs according to a type thereof, and
wherein the number of the magnetic nano particles coupled with the cancer cell corresponds to the number of EpCAMs.

6. The device of claim 1, wherein sensitivity S of the GMR sensor unit and a distance R from a surface of the GMR sensor unit satisfy the following equation:

$$S \propto 1/R^3.$$

7. The device of claim 1, further comprising a selection device connected to one end of the GMR sensor unit,
wherein a unit analysis cell includes the GMR sensor unit and the selection device, and
wherein the analysis device comprises a plurality of unit analysis cells.

8. The device of claim 7, wherein the unit analysis cells are arranged in an array.

9. The device of claim 1, further comprising a channel through which a mixed solution comprising the target particle flows,
wherein the GMR sensor unit and the electrodes are arranged in the channel.

10. The device of claim 9, wherein the mixed solution is blood, and
wherein the target particle is a blood cancer cell.

11. The device of claim 7, wherein the selection device is one of a transistor and a diode.

12. The device of claim 1, wherein the receptors are fastened to only a portion of the receptor-fastened layer, the portion overlapping with the GMR sensor unit.

* * * * *